US006437163B1

(12) United States Patent
Branlard et al.

(10) Patent No.: US 6,437,163 B1
(45) Date of Patent: Aug. 20, 2002

(54) METHOD FOR PREPARING SILICONES WITH ARYLALKYL FUNCTION(S) BY HYDROSILYLATION

(75) Inventors: Paul Branlard; Gérard Mignani; Philippe Olier, all of Lyons; Claudie Willemin, Paris, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/647,995

(22) PCT Filed: Jul. 30, 1998

(86) PCT No.: PCT/FR98/01698

§ 371 (c)(1),
(2), (4) Date: Feb. 23, 2001

(87) PCT Pub. No.: WO99/52965

PCT Pub. Date: Jul. 30, 1998

(30) Foreign Application Priority Data

Apr. 9, 1998 (FR) .............................................. 98/04483

(51) Int. Cl.[7] .................................................. C07F 7/08
(52) U.S. Cl. .......................... 556/450; 556/479; 528/15
(58) Field of Search .......................... 536/479; 556/450; 528/15

(56) References Cited

U.S. PATENT DOCUMENTS 5,248,789 A 9/1993 Wolff

*Primary Examiner*—Paul F. Shaver
(74) *Attorney, Agent, or Firm*—Burns, Doane, Swecker & Mathis, L.L.P.

(57) ABSTRACT

The invention concerns a method for preparing high purity polyorganosiloxanes with arylalkyl function(s) by: hydrosilylation of a hydrogenopolyorganosiloxane, reagent (SiH), and an aromatic monovinyl compound, reagent (Vi), with simultaneous introduction of reagent (SiH) and reagent (Vi), in a reaction medium containing an inert solvent and a hydrosilylation catalyst; then elimination of the solvent, the possible residual reagents (SiH) and (Vi), and/or hydrogenation, the hydrogenation process being optionally followed by an elimination process (or another elimination process) of the products other than polyorganosiloxanes with arylalkyl function(s). The resulting silicones with arylalkyl function(s) can be used as emollients and/or carriers in cosmetic compositions, or as solubilizing agents and emollients in perfume compositions.

25 Claims, No Drawings

METHOD FOR PREPARING SILICONES WITH ARYLALKYL FUNCTION(S) BY HYDROSILYLATION

The present invention relates to a process for preparing silicones containing (an) arylalkyl function(s) of high purity, by hydrosilylation reaction of a hydrogenopolyorganosiloxane and of a monovinylaromatic compound. The silicones containing (an) arylalkyl function(s) of high purity thus obtained can be used as emollients and/or vehicles in cosmetic compositions, and also as solubilizing agents and emollients in fragrancing compositions.

It is known practice to prepare silicones bearing arylalkyl functions by hydrosilylation reaction of a silicone bearing at least one SiH function with an aromatic compound containing a vinyl unsaturation, especially in the presence of a platinum-based catalyst.

The hydrosilylation of aromatic compounds containing vinyl unsaturation can lead to phenomena of radical-mediated polymerization of the said monovinylaromatic compounds, especially at elevated temperature. The use of radical-mediated-polymerization inhibitors, such as phenols or quinones, is often necessary; however, most of these inhibitors are not sufficiently active under hot conditions and require the presence of oxygen to improve their activity.

The Applicant has found an efficient process for the hydrosilylation of monovinylaromatic compounds, which does not require the presence of a radical-mediated-polymerization reaction inhibitor, while at the same time avoiding the risk of such a polymerization reaction.

According to the invention, it is a process for preparing polyorganosiloxanes containing (an) arylalkyl function(s), of high purity, by hydrosilylation reaction of a hydrogenopolyorganosiloxane, reagent (SiH), with a monovinylaromatic compound, reagent (Vi), in the presence of a hydrosilylation catalyst, the said process being characterized in that the hydrosilylation operation is carried out at a temperature from 50° C. to 150° C., preferably from 50° C. to 100° C. and most particularly from 60° C. to 90° C., in the presence of a solvent (S), which is inert with respect to the reagents, having a boiling point at atmospheric pressure of less than 200° C., preferably less than 150° C., by simultaneous introduction of the two reagents (Vi) and (SiH) into the reaction medium comprising the solvent (S) and the hydrosilylation catalyst, this introduction being carried out such that the respective amounts of the two reagents (Vi) and (SiH) corresponding to a reagent (Vi)/reagent (SiH) molar ratio of more than 0.5 to 1.5, preferably of more than 1 to 1.2, and in that at any moment in the hydrosilylation reaction, the amount of reagent (SiH) present, expressed as the mass of SiH functions (29 g per 1 function), corresponds to less than 2% and preferably less than 1% of the reaction mass, excluding the mass of solvent, and in that the hydrosilylation operation is followed by an operation for removal of the solvent (S) and any residual reagents (SiH) and (Vi), and/or by a hydrogenation operation, the said hydrogenation operation optionally being followed by an operation for removal (or a new operation for removal) of the products other than the polyorganosiloxanes containing (an) arylalkyl function(s).

In the definition of a mole of hydrogenopolyorganosiloxane, reagent (SiH), the —SiH function will be considered as the elemental species.

In the definition of a mole of monovinylaromatic compound, reagent (Vi), a gram-molecule of monovinylaromatic compound will be considered as the elemental species.

Among the hydrogenopolyorganosiloxanes, reagents (SiH), which may be used to carry out the process of the invention, mention may be made of those corresponding to the formula (1)

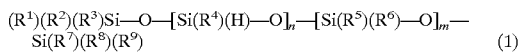

or cyclic homologues thereof, of formula (1) in which the symbols $R^1$ and $R^9$ are identical or different and represent a hydrogen atom or an alkyl radical containing from 1 to 8 carbon atoms, preferably 1 or 2 carbon atoms and most particularly 1 carbon atom, the symbols $R^2$, $R^3$, $R^4$, $R^5$, $R^6$, $R^7$ and $R^8$ are identical or different and represent an alkyl radical containing from 1 to 8 carbon atoms, preferably 1 or 2 carbon atoms and most particularly 1 carbon atom, n is an integer or decimal number which may be from 0 to 10, preferably from 0 to 5, at least one of the radicals $R^1$ and $R^9$ representing a hydrogen atom when n=0, m is an integer or decimal number which may be from 0 to 50, preferably from 0 to 10.

Preferentially, n is equal to 1 and m is equal to 0; in this case, the said reagent (SiH) is a hydrogenoheptaorganotrisiloxane (abbreviated as MD'M), most particularly hydrogenoheptamethyltrisiloxane.

Among the monovinylaromatic compounds, reagents (Vi), which may be used to carry out the process of the invention, mention may be made of those with a boiling point of less than 200° C., preferably less than 150° C., at atmospheric pressure and corresponding to formula (2)

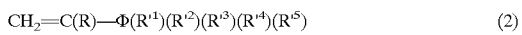

in which formula the symbol Φ represents an aromatic nucleus containing 6 carbon atoms, the symbol R represents H or $CH_3$, the symbols $R'^1$, $R'^2$, $R'^3$, $R'^4$ and $R'^5$ are identical or different and represent H, $CH_3$, F, Cl or Br.

Styrene, α-methylstyrene, α-methylstyrene dimer and pentafluorobenzene may be mentioned preferentially.

Among the solvents (S), inert with respect to the reagents, which may be used to carry out the process of the invention, mention may be made of organic solvents such as toluene, xylene, methylcyclohexane, heptane, octane, etc. and most particularly polyorganosiloxane solvents such as hexamethyldisiloxane.

The hydrosilylation operation is carried out in the presence of a hydrosilylation catalyst; this catalyst is chosen in particular from those based on platinum (0) or on a platinum (0) derivative, such as the platinum complexes described in U.S. Pat. Nos. 3,159,601, 3,159,662, 3,715,334, 3,814,730, etc. A preferred catalyst is the Karstedt catalyst, used for example in a proportion from 1 to 300 parts, preferably from 5 to 100 parts, by mass of platinum per million parts by mass of reagents (SiH) and (Vi) used.

The hydrosilylation operation is preferably carried out at atmospheric pressure.

The introduction of the reagents (SiH) and (Vi) is preferably carried out by simultaneously and continuously adding the two reagents to the reaction mass comprising the solvent and the catalyst.

The addition time is adjusted so as to consume the reagent (Vi) by hydrosilylation gradually as it is introduced. The amount of reagent (Vi) in the medium is thus always low, which limits the risks of a radical-mediated polymerization.

Similarly, the simultaneous introduction of the two reagents and their simultaneous consumption avoids the accumulation of free —(SiH) functions in the medium; the potential exothermicity of the reaction is thus limited.

The use of a radical-mediated polymerization inhibitor is thus unnecessary.

The solvent (S) and the unreacted reagents can then be removed. Their removal can be carried out by distillation under vacuum or reduced pressure (for example from about 1.013 Pa to 101 300 Pa).

This distillation operation can optionally be followed by a hydrogenation operation, so as to remove the remaining unsaturations due to a dehydrogenocondensation reaction. The proportion of compounds whose presence is due to this dehydrogenocondensation reaction increases as the temperature increases. Such compounds are undesirable in applications such as cosmetology or perfumery in particular.

The hydrogenation operation can be carried out at a temperature from about 25° C. to 200° C., preferably from about 50° C. to 150° C., at a hydrogen pressure from about 0 bar to 50 bar, preferably from about 5 bar to 25 bar, in the presence of an effective amount of hydrogenation catalyst.

Among the hydrogenation catalysts which may be mentioned most particularly are platinum and palladium; they can be used in a proportion from 0.01% to 5%, preferably from 0.01% to 1% by weight of metal relative to the mass to be hydrogenated. The catalysts are generally deposited on a carbon black support.

According to one embodiment (which is advantageous in particular for the preparation of silicones containing alkylaromatic functions which are used in cosmetics or perfumery), the medium obtained from the hydrosilylation operation is subjected to a hydrogenation operation under the conditions described above (in order to reduce the amount or to remove the presence of unsaturated compounds resulting from the hydrosilylation reaction) and is then optionally subjected to an operation to remove the products other than the polyorganosiloxanes containing (an) arylalkyl function(s). This removal operation can be carried out by distillation under vacuum or reduced pressure, for example from about 1.013 Pa to 101 300 Pa.

One particular embodiment of the process forming the subject of the invention consists in carrying out the hydrosilylation operation, as described above, using hydrogenoheptamethyltrisiloxane as reagent (SiH), styrene as reagent (Vi) and hexamethyldisiloxane as solvent (S), at a temperature from 50° C. to 150° C., preferably from 50° C. to 100° C. and most particularly from 60° C. to 90° C.

This operation is then followed by an operation for removal under vacuum of the solvent (S) and of the remaining reagents (SiH) and (Vi), followed by a hydrogenation operation and optionally by another distillation operation. The order in which the distillation and hydrogenation operations is carried out can also be reversed.

It is possible for the hydrogenation operation to be carried out only when the hydrosilylation operation has been carried out at a relatively low temperature, for example of about 60° C., or when the reagent (Vi) used does not lead to the presence of unsaturated compounds (this is especially the case for α-methylstyrene).

The product obtained according to the process of the invention, from hydrogenoheptamethyltrisiloxane and styrene, at a hydrosilylation temperature from 50° C. to 100° C., is formed of a mixture consisting:

for more than 70% by mass, generally for at least 75% by mass, of trisiloxane of formula

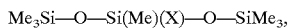

in which X represents a —CH$_2$—CH$_2$—Ph function, for less than 25% by mass, generally from 10% to 20% by mass, of trisiloxane of formula

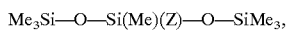

in which Z represents a —CH(CH$_3$)—Ph function, and less than 5% by mass, generally from 0% to 2% by mass, of trisiloxane of formula

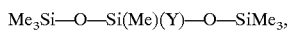

in which Y represents a —CH═CH—Ph function, in which formulae Me represents a methyl radical and Ph represents a phenyl radical.

The silicones containing (an) arylalkyl function(s), of high purity, obtained according to the process of the invention, especially those containing (a) phenylalkyl function(s), most particularly those obtained from hydrogenoheptamethyltrisiloxane and styrene, formed from a mixture consisting:

for more than 70% by mass, generally for at least 75% by mass, of trisiloxane of formula

in which X represents a —CH$_2$—CH$_2$—Ph function, for less than 25% by mass, generally from 10% to 20% by mass, of trisiloxane of formula

in which Z represents a —CH(CH$_3$)—Ph function, and less than 5% by mass, generally from 0% to 2% by mass, of trisiloxane of formula

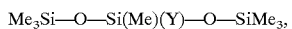

in which Y represents a —CH═CH—Ph function, in which formulae Me represents a methyl radical and Ph represents a phenyl radical, can be used in particular in cosmetic compositions and fragrancing compositions.

They can be used as emollients and/or vehicles and/or transfer-resistant agents in cosmetic compositions. They can at least partially constitute the vehicle for the natural or synthetic active substances present in cosmetic compositions; they can thus at least partially replace the usual lipophilic vehicles. Moreover, they give the said compositions emollient properties and can thus at least partially replace the usual emollients or conditioners, especially the usual silicone oils, in particular such as the polyorganosiloxanes of the phenyltrimethicone or octamethyltetramethicone type.

The amounts of organotrisiloxane containing a phenylalkyl or phenylalkenyl function to be used depend on the desired function and on the type of cosmetic formulation under consideration. A person skilled in the art is capable of determining these amounts.

Mention may thus be made as follows, by way of indication, of the amounts by mass of organotrisiloxane containing a phenylalkyl function that are favourably present in cosmetic compositions as a function of the desired application:

care products (creams, milks, 0.5–5% etc.)
make-up-removing products 1–2%
body products 0.5–1.5%
make-up products (foundations, up to 40% compact powders, mascaras, eyeshadows, lipsticks)
hygiene and toiletry products 1–10% (deodorants, antiperspirants, shaving products and aqueous-alcoholic products)
antisun products (cream, milk, up to 99%, or even oil) more, preferably 10–40%
hair products
  (shampoo, conditioner) up to 5%
  (haircare, hairdressing) up to 10%

The said silicones containing (a) phenylalkyl function(s), especially those prepared from hydrogenoheptamethyltrisiloxane and styrene, can be used as solubilizing agents and emollients in fragrancing compositions.

The said fragrancing compositions can comprise from about
3% to 20% of their weight of a fragrancing base, and
75% to 97% of their weight of a lipophilic solubilizing agent based on the said silicones containing phenylalkyl functions.

The fragrancing base present can be any compound used in the perfumery industry which is responsible for various perfumed notes.

The fragrancing composition is a solution, preferably free of alcohol (ethanol).

According to one embodiment, the said solubilizing agent consists of the said silicones containing phenylalkyl functions combined with at least one other volatile or non-volatile solvent for the fragrancing bases, such as volatile silicones (for example hexamethyldisiloxane), propylene glycol or esters (for example diethylene glycol dioctanoate or diisononanoate).

The said other solvent(s) can be present in a weight ratio of silicones containing phenylalkyl functions/other solvent (s) from about 5/95 to 95/5, preferably from about 10/90 to 90/10, most particularly from about 25/75 to 90/10.

The examples which follow are given for illustrative purposes.

EXAMPLE 1

Hydrosilylation of Styrene with heptamethyltrisiloxane 1803 g (11.12 mol) of hexamethyldisiloxane (HMDS) and 4.15 g of a solution of Karstedt platinum having a titre of 11.5% platinum (0) are introduced, with the aid of a pump, into a 10-liter reactor. The reaction mass is brought to 90° C. and 4150 g (19.3 mol) of heptamethyltrisiloxane (MD'M) and 2207 g (21.22 mol) of styrene are added simultaneously over 5 hours.

The monitoring of the major species by gas chromatography shows that the reaction is virtually quantitative (in % by weight).

| time | HMDS | styrene | MD'M | X-HMTS | Y-HMTS | Z-HMTS |
|------|------|---------|------|--------|--------|--------|
| 1 h  | 54.9 | 0.6     | 1.5  | 30.4   | 0.8    | 5.6    |
| 2 h  | 36.9 | 2.0     | 1.6  | 42.9   | 1.7    | 7.8    |
| 3 h  | 30.3 | 2.3     | 2.1  | 47.7   | 2.5    | 8.3    |
| 4 h  | 24.2 | 2.1     | 2.8  | 53.2   | 3.2    | 9.3    |
| 5 h  | 21.7 | 3.2     | 2.5  | 53.2   | 3.3    | 9.3    |

The content of free styrene in the reaction mass at the end of the reaction represents 88% of the excess styrene employed, which proves that there is very little polymerization. The remainder to 100% consists of the product of reaction of the by-products of the MD'M (MD'DM and MM' in particular) and of the styrene.

In this table,
X-HMTS has the following meaning

Me$_3$Si—O—Si(Me)(X)—O—SiMe$_3$, in which X represents a —CH$_2$—CH$_2$—Ph function
Y-HMTS has the following meaning

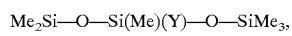
Me$_3$Si—O—Si(Me)(Y)—O—SiMe$_3$, in which Y represents a —CH═CH—Ph function
Z-HMTS has the following meaning

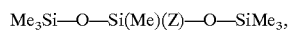
Me$_3$Si—O—Si(Me)(Z)—O—SiMe$_3$, in which Z represents a —CH(CH$_3$)—Ph function
with Me representing methyl and Ph representing phenyl.

Distillation

The reaction mass is then concentrated (evaporation of volatiles at 110° C. under 20 mbar for 7 hours). 5827 g of a coloured product having the composition below (values in % by weight) are collected:

| HMDS | styrene | MD'M | X-HMTS | Y-HMTS | Z-HMTS |
|------|---------|------|--------|--------|--------|
| 0.13 | 0.13    | 0.12 | 77.8   | 4.9    | 14.6   |

Hydrogenation 700 g of this coloured product are loaded into a 1-liter autoclave reactor.

14 g (i.e. 2% by weight) of a platinum catalyst on charcoal having a titre of 2% Pt are introduced. The reaction mass is brought to 100° C. under a pressure of 20 bar of hydrogen. After reaction for three hours with stirring, the reaction mass is cooled and returned to atmospheric pressure. After filtration, 692 g of a colourless product having the composition below are obtained:

| HMDS | styrene | MD'M | X-HMTS | Y-HMTS | Z-HMTS |
|------|---------|------|--------|--------|--------|
| 0.13 | 0       | 0.1  | 80.75  | 1.10   | 14.3   |

After distillation on a column packed with Rashig rings (height=40 cm), 563.3 g (yield 81.4%) of a mixture having the composition below are collected:

| HMDS | styrene | MD'M | X-HMTS | Y-HMTS | Z-HMTS |
|------|---------|------|--------|--------|--------|
| 0    | 0       | 0    | 81.5   | 1.04   | 16.6   |

EXAMPLE 2

Hydrosilylation of Styrene with Heptamethyltrisiloxane 178.9 g (1 mol) of hexamethyldisiloxane and 0.2708 g of a solution of Karstedt platinum having a titre of 11.5% platinum are introduced, with the aid of a pump, into a 1 l reactor. The reaction mass is brought to 60° C. and 250.7 g (1.127 mol) of heptamethyltrisiloxane (OSi) and 128.9 g (1.24 mol) of styrene are added simultaneously over 5 hours.

At the end of the addition, the composition of the reaction mass, analysed by gas chromatography, is as follows (in % by weight):

| HMDS | styrene | MD'M | X-HMTS | Y-HMTS | Z-HMTS |
|------|---------|------|--------|--------|--------|
| 32.9 | 2.69    | 0    | 49.6   | 0.65   | 13.15  |

The content of free styrene corresponds to 96% of the excess styrene employed.

525.3 g of a black product are collected, i.e. a material balance of 97%.

Distillation

The distillation of this crude reaction product on a column packed with Rashig rings (40 cm in height) gives 305.5 g (i.e. a yield of 76.4%) of a mixture having the composition below:

| HMDS | styrene | MD'M | X-HMTS | Y-HMTS | Z-HMTS |
|------|---------|------|--------|--------|--------|
| 0    | 0       | 0    | 77.48  | 0.96   | 21.25  |

It is observed that the content of unsaturated derivative Y-HMTS is close to that obtained in the previous example carried out at 90° C. (hydrosilylation) and including a hydrogenation operation.

A hydrosilylation operation carried out at lower temperature thus makes it possible substantially to reduce the content of unsaturated compound Y-HMTS.

EXAMPLE 3

Hydrosilylation of Heptamethyltrisiloxane and of α-methylstyrene 337 g (2.08 mol) of hexamethyldisiloxane (HMDS) and 0.52 g of a solution of Karstedt platinum having a titre of 11.5% platinum are introduced, with the aid of a pump, into a 2 l reactor. The reaction mass is brought to 90° C. and 444 g (2 mol) of heptamethyltrisiloxane (MD'M) and 259.6 g (2.2 mol) of α-methylstyrene are added simultaneously over 5 hours.

After 24 h, the composition of the reaction mass, analysed by gas chromatography, is as follows (in % by weight):

| HMDS | α-methyl-styrene | MD'M | M-HMTS |
|------|------------------|------|--------|
| 30.1 | 5.17             | 4.36 | 60.8   |

The remainder to 100% consists of the product of reaction of the by-products of MD'M (in particular MD'DM and MM') and of α-methylstyrene.

In this table,

M-HMTS has the following meaning

in which M represents a —CH(CH$_3$)—CH$_2$—Ph function.

After distillation, 569.9 g of a product having a titre of 96% purity of the main compound (yield=81%) are obtained.

EXAMPLE 4

| Fragrancing composition | |
|---|---|
| Lavandin | 7% by weight |
| silicone containing a phenylalkyl function of Example 1, 2 or 3 | 93% by weight |

This composition is obtained by simple mixing of its two constituents.

EXAMPLE 5

| Fragrancing composition | |
|---|---|
| Lavandin | 15% by weight |
| silicone containing a phenylalkyl function of Example 1, 2 or 3 | 50% by weight |
| hexamethyldisiloxane | 35% by weight |

This composition is obtained by simple mixing of its three constituents.

EXAMPLE 6

| Deodorant in the form of a transparent stick | |
|---|---|
| silicone containing a phenylalkyl function of Example 1, 2 or 3 | 9% |
| polypropoxylated myristyl propionate | 70% |
| propylene glycol | 14% |
| triclosan | 0.3% |
| sodium stearate | 6% |
| fragrance | qs |

EXAMPLE 7

| Dry antisun oil | |
| --- | --- |
| silicone containing a phenylalkyl function of Example 1, 2 or 3 | 27% |
| isopropyl palmitate | 25% |
| diisopropyl adipate | 25% |
| Mirasil C-DPDM | 20% |
| octyl methoxycinnamate | 3% |

This composition is obtained by simple mixing of its constituents.

EXAMPLE 8

| Hair lotion for treating the ends of the hair | |
| --- | --- |
| silicone containing a phenylalkyl function of Example 1, 2 or 3 | 5% |
| Mirasil C-DPDM | 90% |
| ethanol | 5% |

This composition is obtained by simple mixing of its constituents.

What is claimed is:

1. A process for preparing polyorganosiloxanes containing (an) arylalkyl function(s), of high purity, by hydrosilylation reaction of a hydrogenopolyorganosiloxane, reagent (SiH), with a monovinylaromatic compound, reagent (Vi) in the presence of a hydrosilylation catalyst, wherein said process comprises
carrying out the hydrosilylation operation
at a temperature from 50° C. to 150° C.,
in the presence of a solvent (S), which is inert with respect to the reagents, having a boiling point at atmospheric pressure of less than 200° C.,
by simultaneous introduction of the two reagents (Vi) and (SiH) into the reaction medium comprising the solvent (S) and the hydrosilylation catalyst, this introduction being carried out such that the respective amounts of the two reagents (Vi) and (SiH) corresponding to a reagent (Vi)/reagent (SiH) molar ration of more than 0.5 to 1.5, and in that at any moment in the hydrosilylation reaction, the amount of reagent (SiH) present, expressed as the mass of SiH functions (29 g per 1 function), corresponds to less than 2% of the reaction mass, excluding the mass of solvent,
and wherein the hydrosilylation operation is followed by an operation for removal of the solvent (S) and any residual reagents (SiH) and (Vi), and/or by a hydrogenation operation, said hydrogenation operation optionally being followed by an operation for removal (or a new operation for removal) of the products other than the polyorganosiloxanes containing (an) arylalkyl function(s).

2. The process according to claim 1, wherein the reagent (SiH) is selected from the reagents of formula (1)

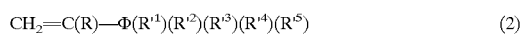

(1)

or cyclic homologues thereof, of formula (1) in which
the symbols $R^1$ and $R^9$ are identical or different and represent a hydrogen atom or an alkyl radical comprising from 1 to 8 carbon atoms, and most particularly 1 carbon atom,
the symbols $R^2$, $R^3$, $R^4$, $R^5$, $R^6$, $R^7$ and $R^8$ are identical or different and represent an alkyl radical containing from 1 to 8 carbon atoms,
n is an integer or decimal number which may be from 0 to 10, at least one of the radicals $R^1$ and $R^9$ representing a hydrogen atom when n=0,
m is an integer or decimal number which may be from 0 to 50.

3. The process according to claim 2, wherein n is equal to 1 and m is equal to 0.

4. The process according to claim 3, wherein the said reagent (SiH) is hydrogenoheptamethyltrisiloxane.

5. The process according to claim 1, wherein the reagent (Vi) is selected from those with a boiling point of less than 200° C., at atmospheric pressure and corresponding to formula (2)

$$CH_2=C(R)-\Phi(R'^1)(R'^2)(R'^3)(R'^4)(R'^5) \qquad (2)$$

in which formula
the symbol $\Phi$ represents an aromatic nucleus containing 6 carbon atoms,
the symbol R represents H or $CH_3$,
the symbols $R'^1$, $R'^2$, $R'^3$, $R'^4$ and $R'^5$ are identical or different and represent H, $CH_3$, F, Cl or Br.

6. The process according to claim 5, wherein the reagent (Vi) is selected from the group consisting of styrene, α-methylstyrene, α-methylstyrene dimer and pentafluorobenzene.

7. The process according to claim 1, wherein the solvent (S) is selected from the group consisting of organic solvents.

8. The process according to claim 1, wherein the introduction of the reagents (SiH) and (Vi) is carried out by simultaneously and continuously adding the two reagents to the reaction mass comprising the solvent and the catalyst.

9. The process according to claim 1, wherein the solvent (S) and the unreacted reagents from the hydrosilylation operation are removed by distillation under vacuum or reduced pressure, and the distillation operation is followed by a hydrogenation operation.

10. The process according to claim 1, wherein the medium obtained from the hydrosilylation operation is subjected to a hydrogenation operation, and then optionally to an operation to remove the products other than the polyorganosiloxanes containing (an) arylalkyl function(s) by distillation under vacuum or reduced pressure.

11. The process according to claim 1, characterized in that the hydrosilylation operation is carried out using hydrogenoheptamethyltrisiloxane as reagent (SiH), styrene as reagent (Vi) and hexamethyldisiloxane as solvent (S), at a temperature from 50° C. to 150° C., and in that it is followed by an operation for removal under vacuum of the solvent (S) and of the remaining reagents (SiH) and (Vi), followed by a hydrogenation operation and optionally by another distillation operation, the order in which the distillation and hydrogenation operations is carried out possibly being reversed.

12. The process according to claim 11, wherein the hydrosilylation operation is carried out at a temperature from 50° C. to 100° C.

13. The process obtained according to the process of claim 12, which it is formed from a mixture comprising:
for more than 70% by mass, of trisiloxane of formula

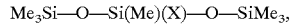

in which X represents a $-CH_2-CH_2-Ph$ function, for less than 25% by mass, of trisiloxane of formula

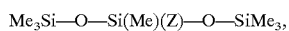

in which Z represents a —CH(CH$_3$)—Ph function,
and less than 5% by mass, generally from 0% to 2% by mass, of trisiloxane of formula

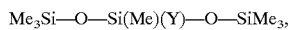

in which Y represents a —CH═CH—Ph function,
in which formulae Me represents a methyl radical and Ph represents a phenyl radical.

14. The process according to claim 1, wherein said temperature is from 50° C. to 100° C.

15. The process according to claim 14, wherein said temperature is from 60° C. to 90° C.

16. The process according to claim 1, wherein said atmospheric pressure is less than 150° C.

17. The process according to claim 1, wherein said reagent (Vi)/reagent (SiH) molar ratio is more than 1 to 1.2.

18. The process according to claim 1, wherein said mass of SiH functions corresponds to less than 1% of the reaction mass.

19. The process according to claim 2, wherein said alkyl radicals comprise 1 or 2 certain atoms.

20. The process according to claim 2, wherein n is from 0 to 5.

21. The process according to claim 2, wherein m is from 0 to 10.

22. The process according to claim 5, wherein said boiling point is less than 150° C.

23. The process according to claim 7, wherein said organic solvent is toluene, xylene, methylcyclohexane, heptane, octane or a polyorganosiloxane.

24. The process according to claim 23, wherein said polyorganosiloxane is hexamethyl disiloxane.

25. The process according to claim 12, wherein said temperature is from 60° C. to 90° C.

* * * * *